United States Patent
Lohman et al.

(10) Patent No.: US 10,597,650 B2
(45) Date of Patent: Mar. 24, 2020

(54) LIGASE ACTIVITY

(71) Applicant: New England Biolabs, Inc., Ipswich, MA (US)

(72) Inventors: Gregory Lohman, Cambridge, MA (US); Thomas C. Evans, Topsfield, MA (US); Larry A. McReynolds, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 1336 days.

(21) Appl. No.: 13/829,489

(22) Filed: Mar. 14, 2013

(65) Prior Publication Data

US 2014/0179539 A1    Jun. 26, 2014

Related U.S. Application Data

(60) Provisional application No. 61/745,244, filed on Dec. 21, 2012.

(51) Int. Cl.
| | | |
|---|---|---|
| *C12N 9/90* | (2006.01) | |
| *C12N 9/00* | (2006.01) | |
| *C12Q 1/6853* | (2018.01) | |
| *C12Q 1/6862* | (2018.01) | |

(52) U.S. Cl.
CPC .............. *C12N 9/93* (2013.01); *C12N 9/00* (2013.01); *C12Q 1/6853* (2013.01); *C12Q 1/6862* (2013.01); *C12Y 605/01003* (2013.01); *C12Q 2521/501* (2013.01); *C12Q 2561/125* (2013.01)

(58) Field of Classification Search
None
See application file for complete search history.

(56) References Cited

U.S. PATENT DOCUMENTS

| | | | |
|---|---|---|---|
| 5,429,807 A | 7/1995 | Matson et al. | |
| 5,599,695 A | 2/1997 | Pease et al. | |
| 5,654,413 A | 8/1997 | Brenner et al. | |
| 5,871,928 A | 6/1999 | Fodor et al. | |
| 6,368,801 B1 | 4/2002 | Faruqi | |
| 7,361,488 B2 | 4/2008 | Fan et al. | |
| 7,888,015 B2 | 2/2011 | Toumazou et al. | |
| 2010/0184618 A1* | 7/2010 | Namsaraev | C12Q 1/6837 506/9 |
| 2011/0092375 A1 | 4/2011 | Zamore et al. | |

FOREIGN PATENT DOCUMENTS

WO        WO0179420        8/1998

OTHER PUBLICATIONS

Sriskanda et al., Nucleic Acids REsearch, 1998, vol. 26, pp. 3536-3541.*
Nilsson et al., Nature Biotechnology, 2000, vol. 18 pp. 791-793.*
Ho et al., Journal of Virology, 1997, vol. 71, pp. 1931-1937.*
Nilsson et al., Nucleic Acids Research, 2001, vol. 29, pp. 578-581.*
Sriskanda et al., Nucleic Acids Research, 1998, col. 26, pp. 3536-3541.*
Odell, et al, J. Biol. Chem., 274, 14032-14039, 1999.
Nilsson, et al, Nucleic Acids Research, 29, 2, 578-581, 2001.
Lohman, et al, Nucleic Acids Research, 42, 3, 1831-1844, 2014.
International Search Report for International Application No. PCT/US2013/076684, dated Mar. 19, 2014.
Yeakley, et al., Nat Biotechnol., 20(4):353-8 (2002).
Bullard and Bowater, Biochem. J., 398(1):135-44 (2006).
Li, et al., Curr Protoc Mol Biol. Apr; Chapter 4: Unit 4.13.1-9 (2012).
Li, et. al., Anal. Chem., 81 (12):4906-4913 (2009).
Absalan and Ronaghi, Methods in Molecular Biology, 396:315-330 (2007).
Nilsson, et al., Nature Biotechnology, 18:791-793 (2000).
Nilsson, et al., Science, 265, 2085-2088 (1994).
Nilsson, et al., Nat Genet. 16:252-255 (1997).
Barany, PCR Methods Appl., 1:5-16 (1991).
Landegren, Bioessays 15:761-765 (1993).
Wiedmann, et al., PCR Methods Appl. 3:S51-64 (1994).
Baner, et al., Nucleic Acids Res. 26:5073-5078 (1998).
Hardenbol, et al., Nature Biotechnol. 21:673-678 (2003).
Landegren, Methods Cell Biol. 75:787-797 (2004).
Sriskandas, et al., Nucleic Acid Research, 26:3536-3541 (1998).
Ho, et al., J. Virol., 71(3):1931 (1997).
Nair, et al., Nat. Struct. Mol. Biol., 14:770-778 (2007).
Nandakumar, Mol. Cell, 26:257-271 (2007).
Pascal, et al., Nature, 432:473-478 (2004).
Pease, et al., Proc. Natl. Acad. Sci. USA, 91(11):5022-5026 (1994).
Khrapko, et al., Mol Biol (Mosk) (USSR) 25:718-730 (1991).
Stimpson, et al., Proc. Natl. Acad. Sci. USA, 92:6379-6383 (1995).
Guo, et al., Nucleic Acids Res. 22:5456-5465 (1994).
Peng, et al., Anal Chem., 82(23):9727-35 (2010).
Syvanen, Nat Genet., 37 Suppl:S5-10, (2005).
Lu, et al., Biocimica et Biophysica Acta, 1701:37-48 (2004).
Notomi, et al., Nucleic Acids Research, 28(12):e63 (2000).
Mori, et al. Biochem. Biophys. res. Commun., 289:150-154 (2001).
Tomita, et al., Nat. Protocols, 3(5):877-82 (2008).
Goto, et al., BioTechniques, 46(3):167-71 (2009).
Gandelman, et al., PLoS One, 5:e14155 (2010).
Pourmand, et al., PNAS, 103(17):6466-70 (2006).
http://www.ncbi.nlm.nih.gov/projects/genome/probe/doc/TechMIP.shtml.

(Continued)

*Primary Examiner* — Mindy G Brown
(74) *Attorney, Agent, or Firm* — New England Biolabs, Inc; Harriet M. Strimpel

(57) ABSTRACT

Compositions and methods are provided for ligating polynucleotides having a length that is greater than 8 nucleotides on an RNA splint. The ligation reaction provides consistent results in high or low ATP concentrations. The reaction can occur rapidly and is generally at least 10 fold more efficient than T4DNA ligase under optimal conditions for T4DNA ligase and the reaction time is less than 6 hours for example, less than 1 hour.

14 Claims, 11 Drawing Sheets

Specification includes a Sequence Listing.

(56) References Cited

OTHER PUBLICATIONS

Lohman et al, Nucleic Acids Res. 2014 42:1831-44.
Odell et al, Nucleic Acids Res. 2003 31: 5090-100.
Sriskanda et al, Nucleic Acids Res. 2002 30: 903-11.
Sriskanda et al, J Biol Chem. 2002 277: 9661-7.
Odell et al, Mol Cell. 2000 6: 1183-93.
Sriskanda et al, Nucleic Acids Res. 1999 27: 3953-63.
Sriskanda et al, Nucleic Acids Res. 1998 26: 4618-25.
Sriskanda et al, Nucleic Acids Res. 1998 26: 3536-41.
Sriskanda Nucleic Acids Res. 1998 26:505-31.
Doherty, et al., Structural and mechanistic conservation in DNA ligases, Nucl. Acids Res. (2000) 28 :4051-4058.
Martin, et al., ATP-dependent DNA ligases, Genome Biol. 2002; 3: 3005.1-3005.7.
Ellenberger, et al., Eukaryotic DNA Ligases: Structural and Functional Insights, Annu Rev Biochem. 2008; 77: 313-338.

* cited by examiner

FIG. 4
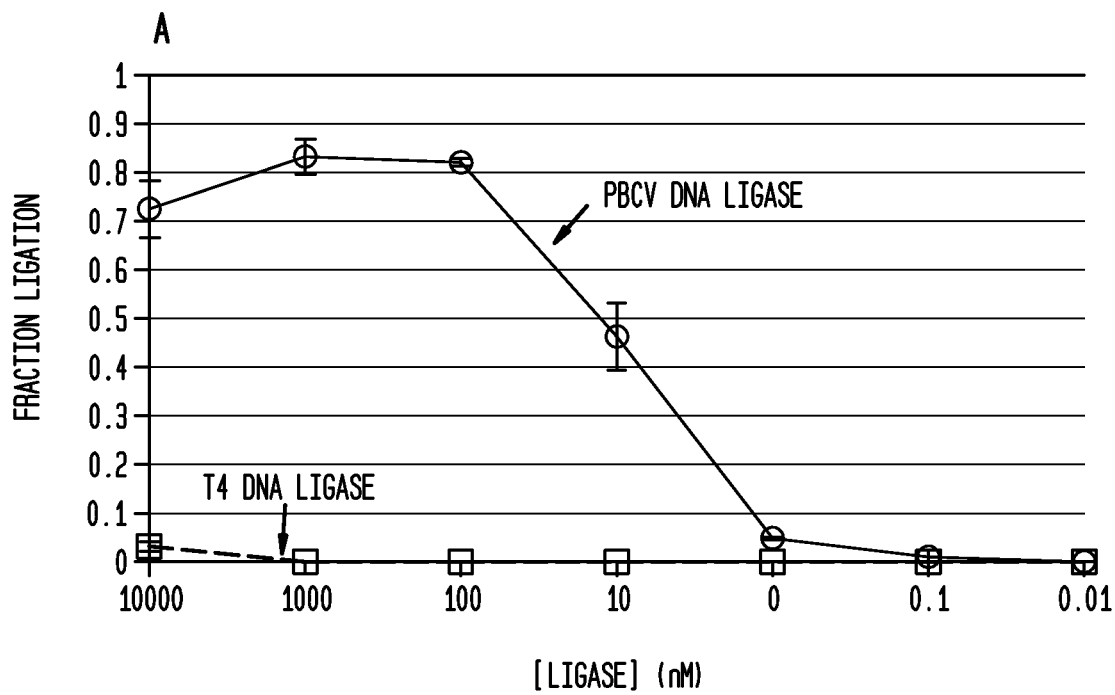
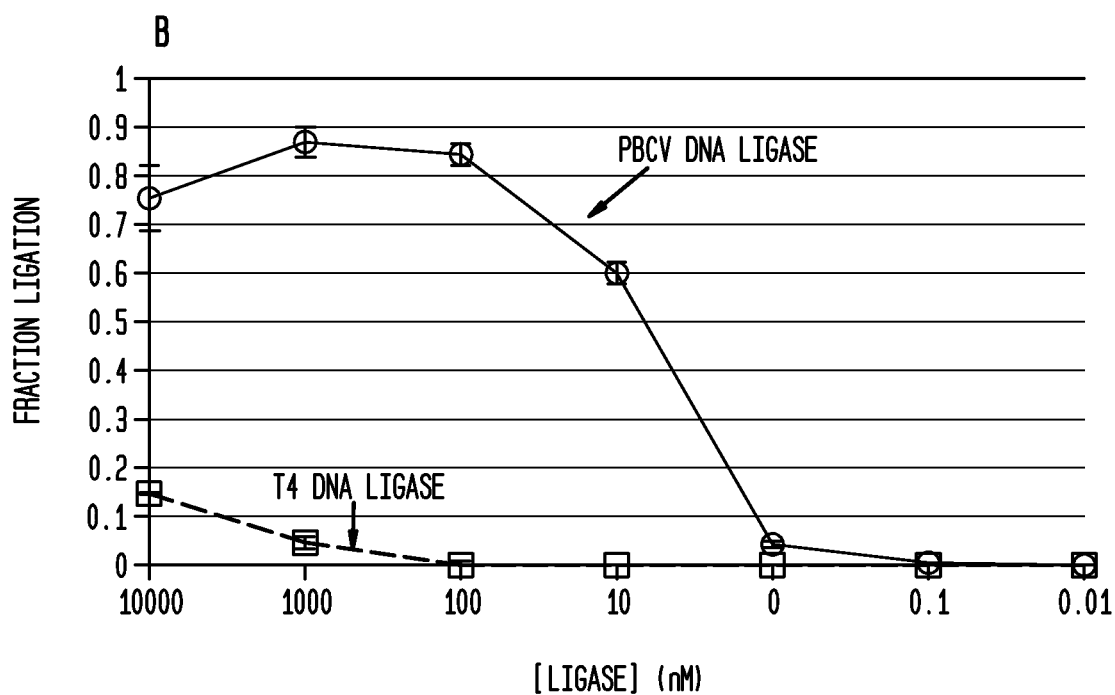

FIG. 7
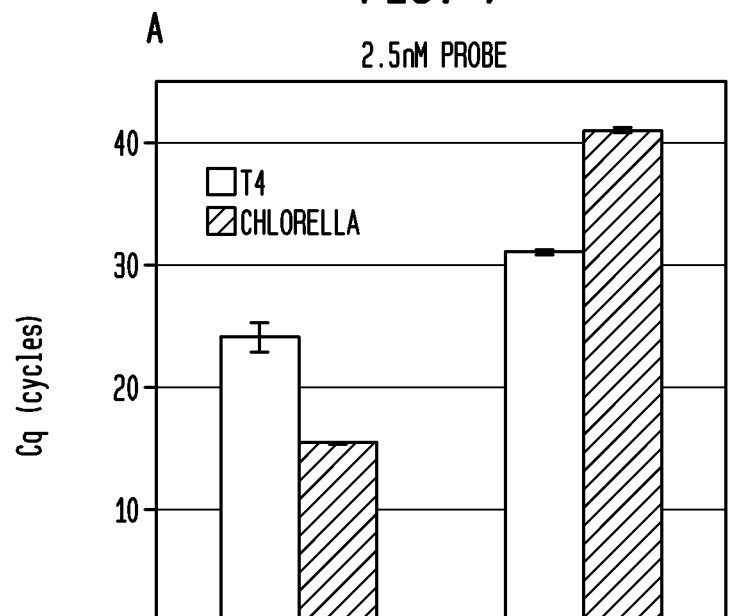
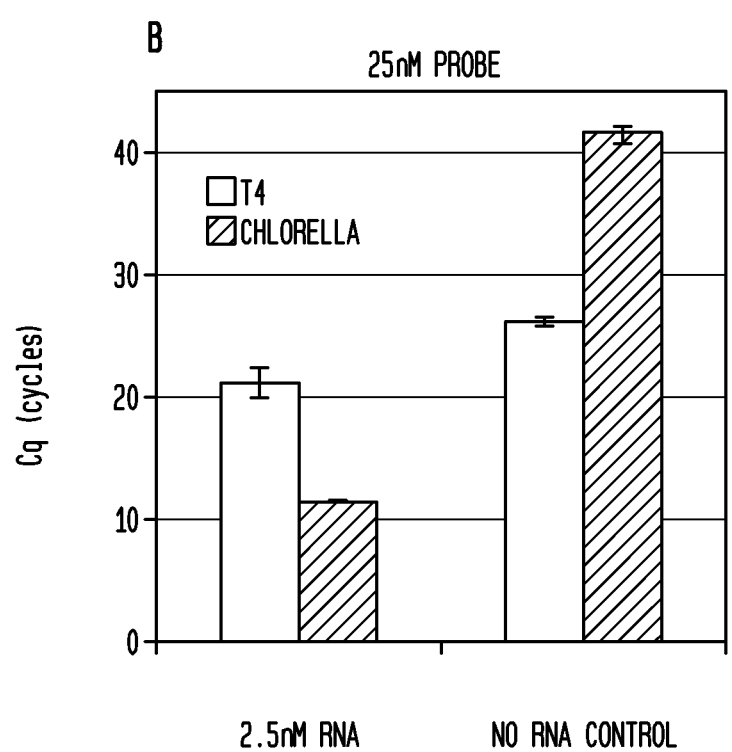

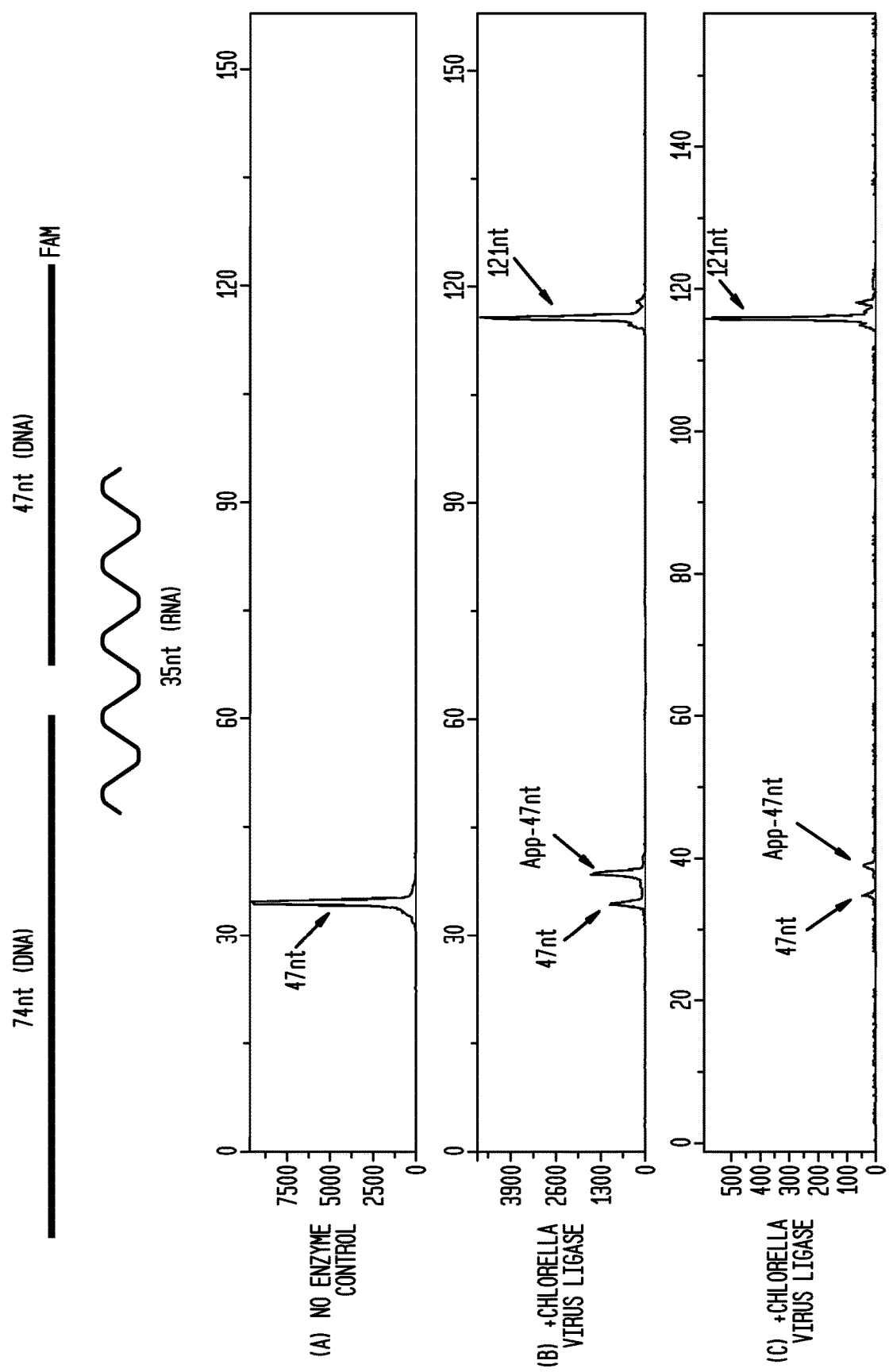

FIG. 9

MAITKPLLAATLENIEDVQFPCLATPKIDGIRSVKQTQMLSRTFKPIRNSVMNRLLTELLPEGSDGEISIEGATFQDTTSAVMTGH
KMYNAKFSYYWFDYVTDDPLKKYIDRVEDMKNYITVHPHILEHAQVKIIPLIPVEINNITELLQYERDVLSKGFEGVMIRKPDGKY
KFGRSTLKEGILLKMKQFKDAEATIISMTALFKNTNTKTKDNFGYSKRSTHKSGKVEEDVMGSIEVDYDGVVFSIGTGFDADQRRD
FWQNKESYIGKMVKFKYFEMGSKDCPRFPVFIGIRHEEDR (SEQ ID NO: 1)

5'-TATAACTTTACTTCTATTGC (SEQ ID NO: 2)

pTGATGGGACCTACAATGTACCAGAAGCGTC-FAM (SEQ ID NO: 3)

5'GACGCUUCUGGUACAUUGUAGGUCCCAUCAGCAAUAGAAGUAAAGUUAUA (SEQ ID NO: 4)

SEQUENCE LISTING

<160> NUMBER OF SEQ ID NOS: 13

<210> SEQ ID NO 1
<211> LENGTH: 298
<212> TYPE: PRT
<213> ORGANISM: Chlorella virus

<400> SEQUENCE: 1

```
Met Ala Ile Thr Lys Pro Leu Leu Ala Ala Thr Leu Glu Asn Ile Glu
1               5                  10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Asp Pro Leu Lys Lys Tyr Ile Asp Arg
            100                 105                 110

Val Glu Asp Met Lys Asn Tyr Ile Thr Val His Pro His Ile Leu Glu
        115                 120                 125

His Ala Gln Val Lys Ile Ile Pro Leu Ile Pro Val Glu Ile Asn Asn
    130                 135                 140

Ile Thr Glu Leu Leu Gln Tyr Glu Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

Ala Glu Ala Thr Ile Ile Ser Met Thr Ala Leu Phe Lys Asn Thr Asn
        195                 200                 205

Thr Lys Thr Lys Asp Asn Phe Gly Tyr Ser Lys Arg Ser Thr His Lys
    210                 215                 220
```

```
Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
            260                 265                 270

Phe Lys Tyr Phe Glu Met Gly Ser Lys Asp Cys Pro Arg Phe Pro Val
        275                 280                 285

Phe Ile Gly Ile Arg His Glu Glu Asp Arg
        290                 295

<210> SEQ ID NO 2
<211> LENGTH: 20
<212> TYPE: DNA
<213> ORGANISM: Unknown
<220> FEATURE:
<223> OTHER INFORMATION: Oligonucleotide substrate

<400> SEQUENCE: 2
tataacttta cttctattgc                                              20

<210> SEQ ID NO 3
<211> LENGTH: 30
<212> TYPE: DNA
<213> ORGANISM: Unknown
<220> FEATURE:
<223> OTHER INFORMATION: Oligonucleotide substrate

<400> SEQUENCE: 3
tgatgggacc tacaatgtac cagaagcgtc                                   30

<210> SEQ ID NO 4
<211> LENGTH: 50
<212> TYPE: RNA
<213> ORGANISM: Unknown
<220> FEATURE:
<223> OTHER INFORMATION: Synthetic construct

<400> SEQUENCE: 4
gacgcuucug guacauugua ggucccauca gcaauagaag uaaaguuaua             50

<210> SEQ ID NO 5
<211> LENGTH: 37
<212> TYPE: DNA
<213> ORGANISM: Unknown
<220> FEATURE:
<223> OTHER INFORMATION: Probe

<400> SEQUENCE: 5
cggtaagacc tttcggtact agatcggaag agcacac                           37

<210> SEQ ID NO 6
<211> LENGTH: 37
<212> TYPE: DNA
<213> ORGANISM: Unknown
<220> FEATURE:
<223> OTHER INFORMATION: Probe

<400> SEQUENCE: 6
ggaagccttg gcttttggaa cgttgcgtcg agttttc                           37

<210> SEQ ID NO 7
<211> LENGTH: 17
```

-continued

<212> TYPE: DNA
<213> ORGANISM: Unknown
<220> FEATURE:
<223> OTHER INFORMATION: Primer

<400> SEQUENCE: 7
gtgtgctctt ccgatct                                                17

<210> SEQ ID NO 8
<211> LENGTH: 17
<212> TYPE: DNA
<213> ORGANISM: Unknown
<220> FEATURE:
<223> OTHER INFORMATION: Primer

<400> SEQUENCE: 8
ggaagccttg gcttttg                                                17

<210> SEQ ID NO 9
<211> LENGTH: 22
<212> TYPE: RNA
<213> ORGANISM: Artificial Sequence
<220> FEATURE:
<223> OTHER INFORMATION: Synthetic construct

<400> SEQUENCE: 9
uggaguguga cauugguguu ug                                          22

<210> SEQ ID NO 10
<211> LENGTH: 32
<212> TYPE: DNA
<213> ORGANISM: Artificial Sequence
<220> FEATURE:
<223> OTHER INFORMATION: Probe

<400> SEQUENCE: 10
gtcacactcc tctgagtcgg agacacgcag gg                               32

<210> SEQ ID NO 11
<211> LENGTH: 33
<212> TYPE: DNA
<213> ORGANISM: Artificial Sequence
<220> FEATURE:
<223> OTHER INFORMATION: Probe

<400> SEQUENCE: 11
cctctctatg ggcagtcggt gataaacacc att                              33

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ccatctcatc cctgcgtgtc tccgactcag                                  30

<210> SEQ ID NO 13
<211> LENGTH: 41
<212> TYPE: DNA
<213> ORGANISM: Artificial Sequence
<220> FEATURE:
<223> OTHER INFORMATION: Primer

```
<400> SEQUENCE: 13
ccactacgcc tccgctttcc tctctatggg cagtcggtga t                                41
```

LIGASE ACTIVITY

CROSS REFERENCE

This application claims right of priority to provisional patent application serial number U.S. 61/745,244 filed Dec. 21, 2012.

BACKGROUND

Ligation of single stranded (ss) DNA oligonucleotides splinted by complementary RNA is an essential step in techniques such as RNA-mediated annealing, selection, and ligation (RASL). T4 DNA ligase has been used for RASL as well as for other RNA analysis and detection techniques such as molecular inversion probes, modified ligase chain reactions and ligase detection reactions (for example, Yeakley, et al., *Nat Biotechnol.,* 20(4):353-8 (2002), Bullard and Bowater, *Biochem. J.,* 398(1):135-44 (2006); Li, et al., *Curr Protoc Mol Biol.* April; Chapter 4: Unit 4.13.1-9 (2012); US published application No. 2011/0092375, U.S. Pat. No. 7,361,488; Nilsson, et al., *Nature Biotechnology,* 18:71 (2000); Nilsson, et al., *Science,* 265, 2085-2088 (1994); Barany, *PCR Methods Appl.,* 1:5-16 (1991); Landegren, *Bioessays,* 15:761-765 (1993); Wiedmann, et al., *PCR Methods Appl.,* 3:S51-64 (1994); Nilsson, et al., *Nat Genet.,* 16:252-255 (1997); Baner, et al., *Nucleic Acids Res.,* 26:5073-5078 (1993); Hardenbol, et al., *Nature Biotechnol.,* 21:673-678 (2003); and Landegren, *Methods Cell Biol.,* 75:787-797 (2004)).

T4 DNA ligase works poorly requiring, for example, long incubation times, high concentrations of ligase, and low ATP concentrations to overcome the preferential formation of adenylated DNA side product to accomplish ligation.

T4 RNA ligase was tested as an alternative choice for joining DNA strands hybridized to an RNA template or splint (U.S. Pat. No. 6,368,801). The NAD+ dependent ligase from *Melanoplus sanguinipes* entomopoxvirus was reported to have a ligation activity for DNA hybridized to RNA similar to T4 DNA ligase but only in the presence of $Mn^{2+}$ (Lu, et al., *Biocimica et Biophysica Acta,* 1701:37-48 (2004)). Sriskanda, et al., *Nucleic Acid Research,* 26 (15): 3536-3541 (1998) reported PBCV-1DNA ligase from *Chlorella* where experimental data showed that this ligase could ligate oligonucleotides on a DNA template or DNA splint but could not ligate oligonucleotides on an RNA template or RNA splint. These results were explained by crystal structure studies where the authors showed that PBCV-1 ligase forced the substrate into an RNA-type A-form helix on one side of a nicked substrate, but required a DNA-type B-form helix on the side of the nick providing the 5' phosphate (Ho, et al., *J. Viral.,* 71(3):1931 (1997); Sriskanda, et al., (1998); Nair, et al., *Nat. Struct. Mol. Biol.,* 14:770-778 (2007)). Similar results were reported in crystal structures of the NAD-dependent *E. coli* DNA ligase (Nandakumar, *Mol. Cell,* 26:257-271 (2007)) and human DNA ligase 1 (Pascal, et al., *Nature,* 432:473-478 (2004)) leading to a conclusion that these ligases could not accept RNA-splinted DNA as ligation substrates.

SUMMARY

In general in one aspect, a composition is provided that includes an RNA splint ligase and at least one polynucleotide having a length of at least 8 nucleotides in a buffer.

Embodiments of the composition may include one or more of the following features: the RNA splint ligase and the at least one polynucleotides are in a molar ratio of greater than 100:1 or less than 100:1, 10:1 or 1:1 of ligase to polynucleotide; the buffer comprises 1 µM-1.5 mM ATP, and/or the RNA splint ligase is PBCV-1 ligase.

In general, in one aspect, a method is provided for ligating single stranded polynucleotide fragments, that includes: combining at least two single stranded polynucleotide fragments having complementary regions at a splice junction to an RNA splint and an RNA splint ligase; and permitting the at least two single stranded polynucleotides to ligate to form a single polynucleotide.

Embodiments of the method may include one or more of the following features: performing the ligation reaction in a buffer containing at least 1 µM-1.5 mM ATP; utilizing an RNA splint having a length greater than 8 nucleotides and a plurality of polynucleotides each having a length of greater than 8 nucleotides incubating the reaction for less than 6 hours to achieve at least 70%-90% ligation of polynucleotides; incubating the reaction for less than 1 hour to achieve at least 70%-90% ligation of polynucleotides; and/or performing the ligation reaction with an enzyme:substrate molar ratio of greater than 100:1 or less than 100:1, 10:1 or 1:1. In certain embodiments, the ligation may occur more rapidly for RNA splint ligase than for a ligation using T4 DNA ligase under similar conditions; the single stranded polynucleotide may be a template for quantitative PCR such that amplifying the ligated single stranded polynucleotide results in less background amplification of non-template polynucleotide than observed when the RNA splint ligase is replaced with T4 DNA ligase and/or the splint ligase is capable of ligating the polynucleotides at a rate that is at least 5 times or 10 times faster than T4 DNA ligase under the same reaction conditions and with the same polynucleotides.

In general, in another aspect, a method is provided for analyzing mRNA for its splicing history, comprising: identifying splice junctions, splicing variants or mutations at the splice junction by combining ssDNA oligonucleotides with the mRNA and an RNA splint ligase.

In general in another aspect, a method is provided for detecting RNA sequences that includes: annealing polynucleotides having regions that are complementary at a ligation junction to a splint RNA; ligating the polynucleotides using an RNA splint ligase, amplifying the ligation product; and detecting and optionally quantifying the amplification product.

Embodiments of the method may include one or more of the following features: the RNA sequence is a microRNA; and/or the RNA splint ligase is PBCV-1 ligase.

Panel 2(A) and 2(B): Two DNA oligonucleotides were hybridized to a DNA 2(A) and 2(B) where the peak corresponds to complete ligation.

Panel 2(C) and 2(D): Two DNA oligonucleotides were hybridized to an RNA reverse complement. A peak corresponding to complete ligation was seen only from the reaction using PBCV-1 ligase 2(D) while no ligation was seen using T4 DNA ligase 2(C).

Figure 3:
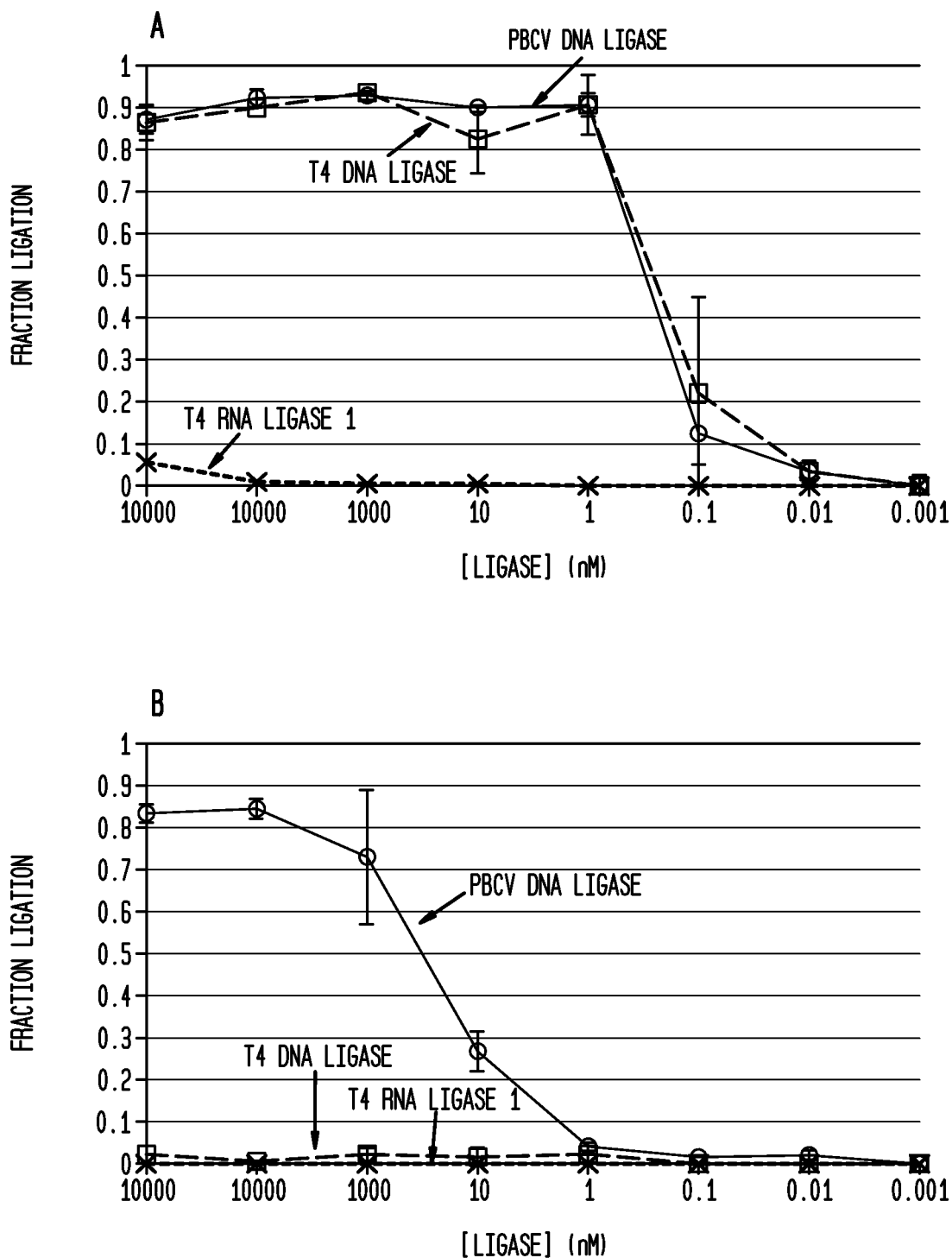

FIG. 3(A)-3(B) shows ligation of 100 nM pre-annealed standard oligonucleotide substrates splinted by DNA using T4 DNA ligase, T4 RNA ligase 1 or PBCV ligase, at a range of concentrations (1 pM-10 µM) at 20° C. in standard ligation buffer containing 1 mM ATP.

3(A) DNA-DNA: ligation splinted by DNA.

3(B) DNA-DNA: ligation splinted by RNA reverse complements.

Both PBCV-1 DNA ligase and T4 DNA ligase could ligate DNA oligonucleotides splinted by DNA with similar ligation activity but only PBCV-1 ligase could form detectable amounts of ligation product for oligonucleotide substrates splinted by RNA reverse complements. T4 RNA Ligase 1 had slight activity on DNA splinted ligation and no detectable activity on RNA splinted ligations.

FIG. 4(A)-4(B) shows ligation of the same oligonucleotide substrates splinted by RNA reverse complements using T4 DNA ligase and PBCV-1 ligase, at a range of concentrations (1 pM-10 µM) at 20° C. in standard ligation buffer containing either 1 mM ATP or 10 µM ATP and 100 nM pre-annealed nicked substrates.

4(A): DNA-DNA ligation splinted by RNA reverse complements in the presence of 1 mM ATP.

4(B): DNA-DNA ligation splinted by RNA reverse complements in the presence of 10 µM ATP.

PBCV-1 ligase ligated DNA oligonucleotides splinted by RNA in buffers containing 1 mM ATP or 10 µM ATP with similar ligation activity. T4 DNA ligase had improved activity at 10 µM ATP only but that activity was at least 5 fold, 10-fold, 20 fold, -50 fold or 100 fold less than that of PBCV-1 ligase under the same conditions. PBCV-1 ligase but not T4 DNA ligase could ligate detectable amounts of oligonucleotide substrates splinted by RNA reverse complements in buffers containing high ATP concentrations.

Figure 5:
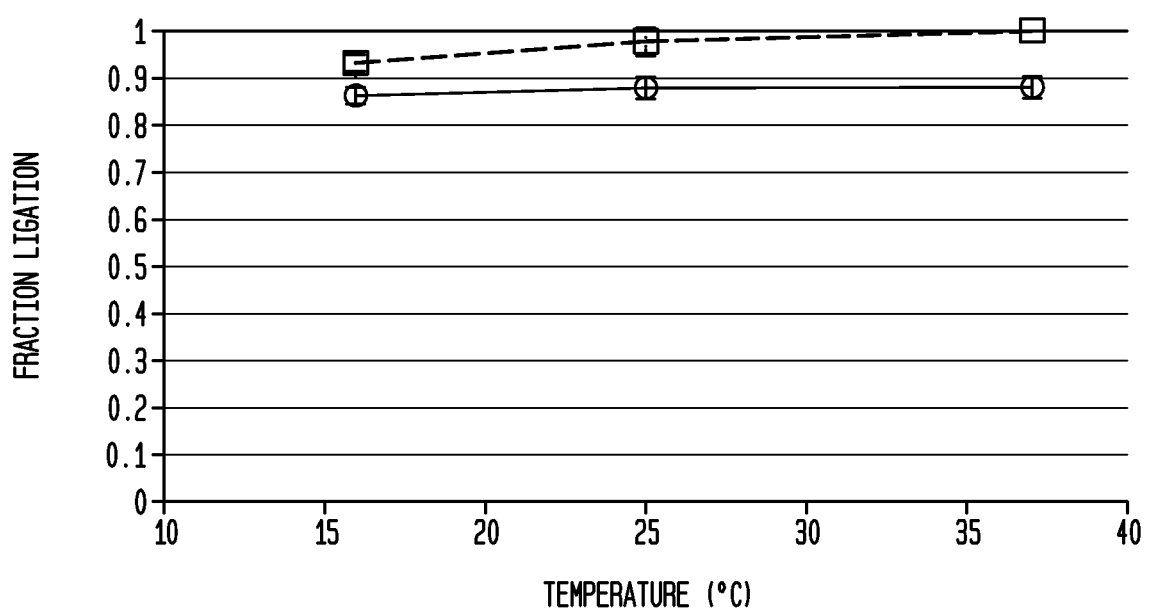

FIG. 5 shows PBCV-1 ligase RNA-splinted DNA ligation activity at multiple temperatures. DNA-DNA ligation splinted by two different RNA templates was conducted at 16° C.; 25° C.; and 37° C. The first DNA oligonucleotides and their reverse complement were standard templates as described in FIG. 9 (square) and a second template having the sequence described in the Sriskanda, et al., (1998) (circles) was also used showing that the sequence had little or no effect on ligation. Reaction conditions were 1 µM PBCV-1 ligase, 250 nM RNA-splinted oligonucleotide substrate in standard ligase buffer for 30 minute incubation.

Figure 6:
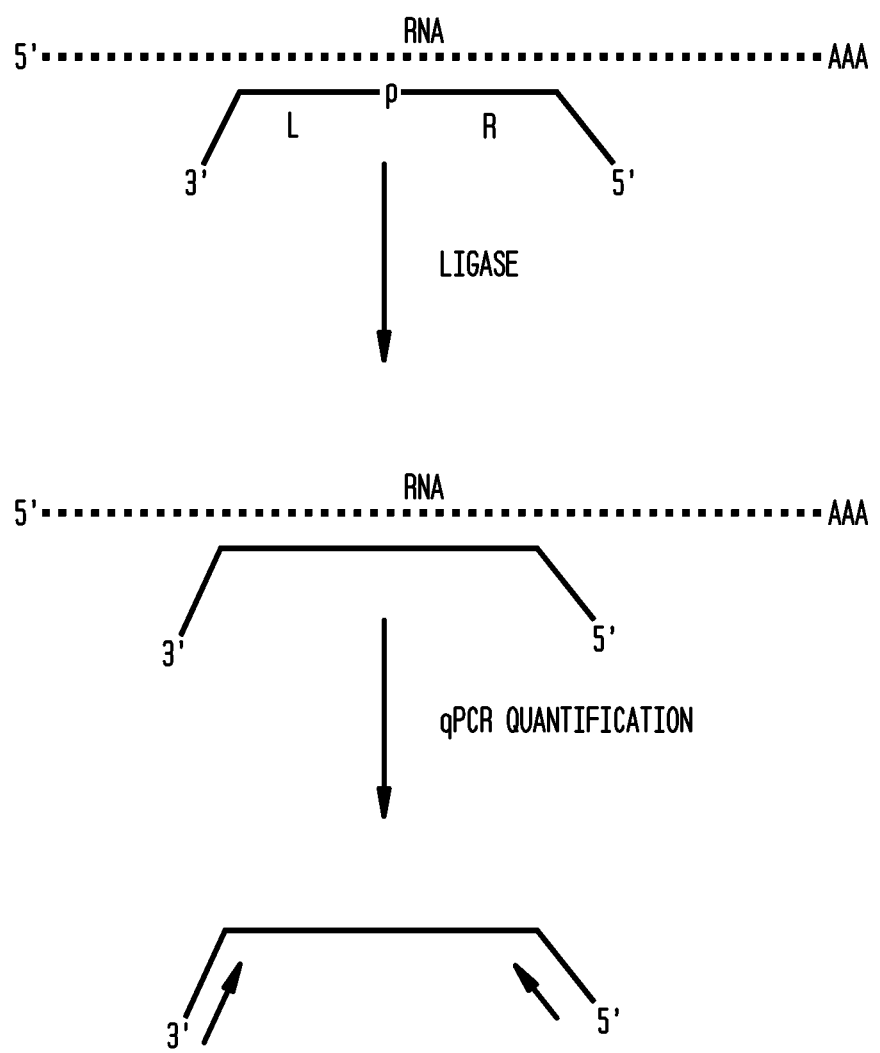

FIG. 6 shows qPCR-detected RASL assay design using an RNA splint ligase. DNA probes were designed to have a region complementary to the RNA target and a qPCR priming region. Correctly annealed probes form a backbone-nick with no gaps, ligatable by an RNA splint ligase. Successful ligation in the presence of probe generates an amplifiable DNA sequence that can be quantified by qPCR.

Figure 1:
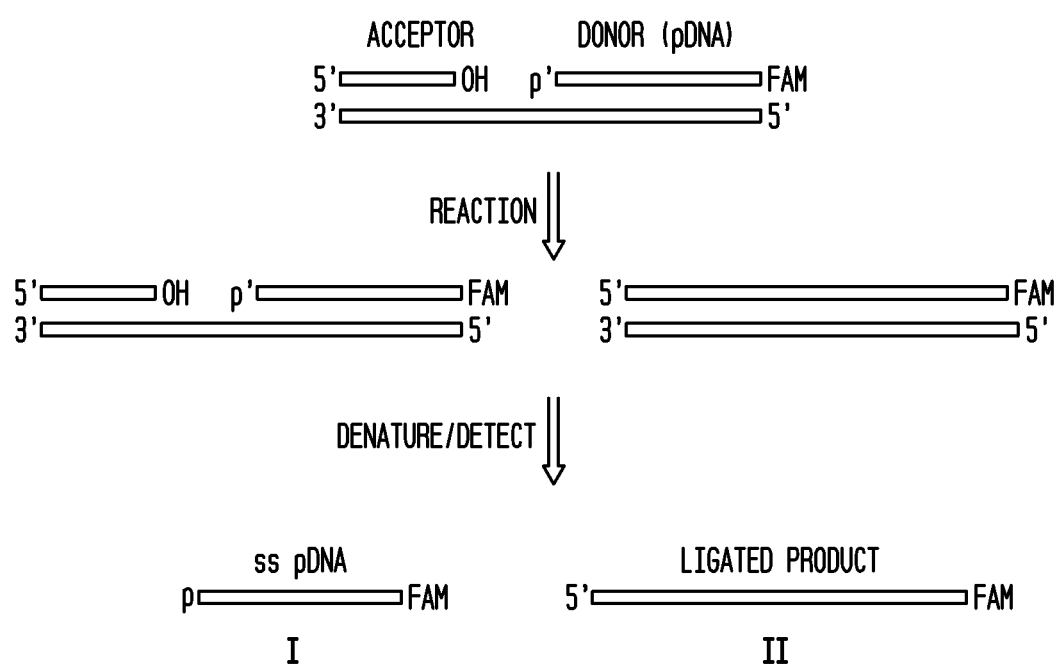
FIG. 1 outlines an assay for ligation of DNA splinted by a DNA or RNA templates. Pre-annealed nicked substrates, such as a 20 deoxynucleotide acceptor DNA, a 30 deoxynucleotide, FAM-tagged and 5'-phosphorylated donor DNA, and either a DNA or an RNA reverse complement (splint), is incubated with a suitable ligase, then quenched with 100 mM EDTA and denatured with formamide. Fragments can be separated and the FAM labeled ssDNA ligation product detected by capillary electrophoresis.
Figure 2:
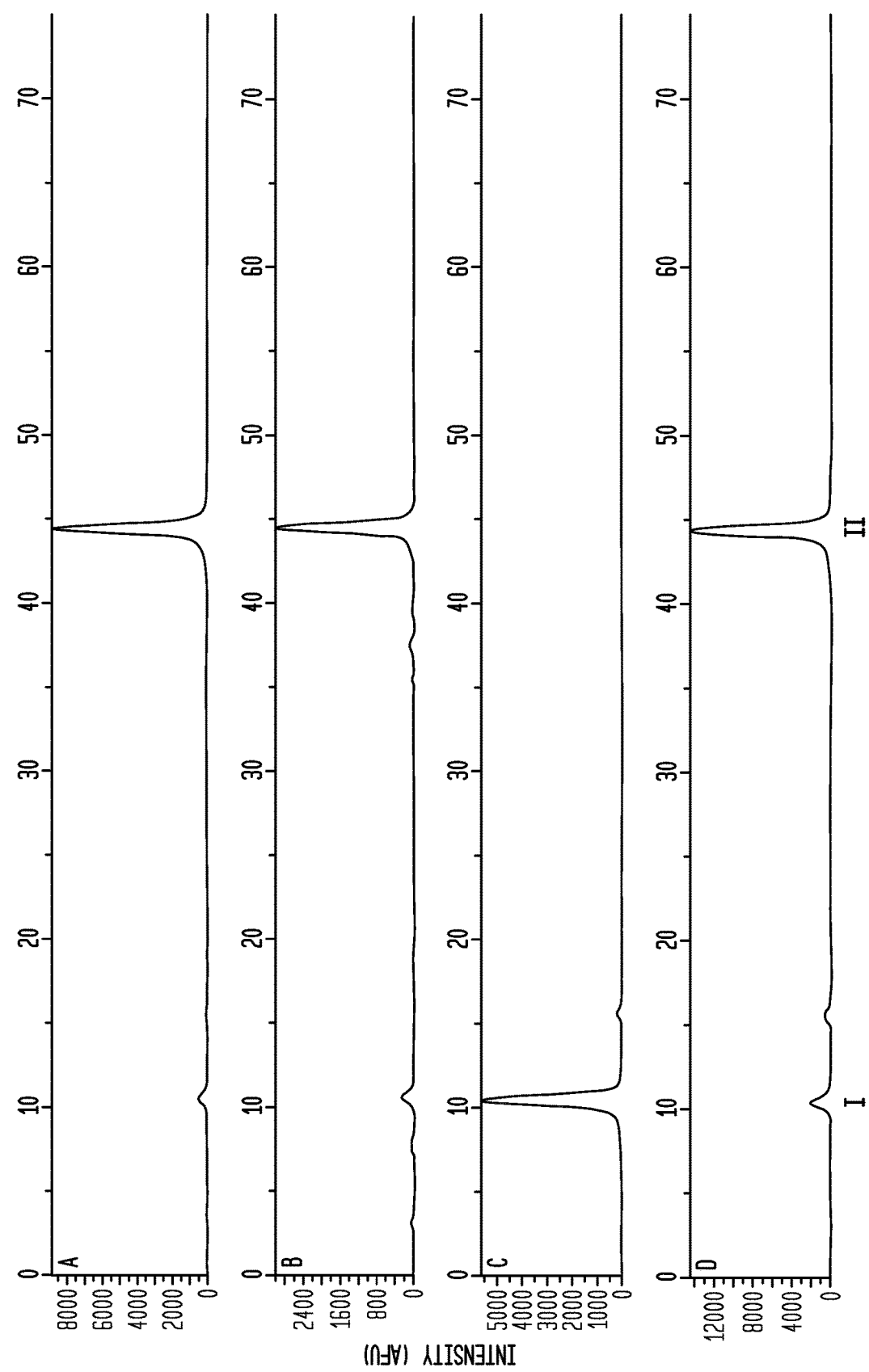
FIG. 2(A)-2(D) shows ligation of two DNA oligonucleotides (DNA-DNA ligation) splinted by DNA or RNA. The marked peaks are unreacted pDNA (I) and ligated product (II) as identified by co-elution with authentic standards. 100 nM of standard oligonucleotides were reacted with 100 nM PBCV-1 DNA ligase (2(B) and 2(D)) or 100 nM T4 DNA ligase (2(A) and 2(C)) for 30 minutes at 20° C.

FIG. 7(A)-7(B) shows results of a RASL assay using PBCV-1 ligase or T4 DNA ligase on ssDNA oligonucleotide substrates as described in FIG. 1 to determine background signal and rate of reaction.

FIG. 7(A): 2.5 nM luciferase mRNA splint.

FIG. 7(B): 25 nM luciferase mRNA splint.

PBCV-1 ligase gave a positive signal at a faster rate than T4 DNA ligase in the presence of RNA substrate as shown by the faster Cq values. Additionally, the background response was significantly delayed with the PBCV-1 ligase as compared with T4 DNA ligase as shown by the higher Cq values when no template RNA was provided.

FIG. 8(A)-8(C): Synthesis of long ssDNA by RNA-mediated splint ligation using PBCV-1 ligase.

A ssDNA of 121 nt was efficiently assembled using two small pieces of ssDNA with a ssRNA splint. The RNA splint was then removed with RNase H, and the ssDNA purified with HPLC. Ligation reactions were performed containing 0.25 µM annealed oligonucleotides and 1.45 µM PBCV-1 ligase in a ligase reaction buffer (66 mM Tris-HCl, 10 mM $MgCl_2$, 1 mM ATP, 1 mM DTT, 7.5% PEG 6000), pH 7.6 at 25° C. Reactions were incubated at 25° C. for 30 minutes (Panel 8(B)) or 16° C. overnight (Panel 8(C)). A no-enzyme control was shown in Panel 8A.

When compared to the standard chemical synthesis method, synthesis of long ssDNA by splint ligation enzymatically has the advantage of high purity, simplified purification, and substantial decrease in cost. These results contrast with current phosphoramidite technology with 99.5% coupling efficiency where a crude solution of synthesized 150-mers would contain 47% full-length product and 53% failure sequences.

FIG. 9 shows the amino acid sequence for *Chlorella* virus polynucleotide ligase (PBCV-1 ligase) and a standard ss oligonucleotide substrate used in the examples.

Figure 10:
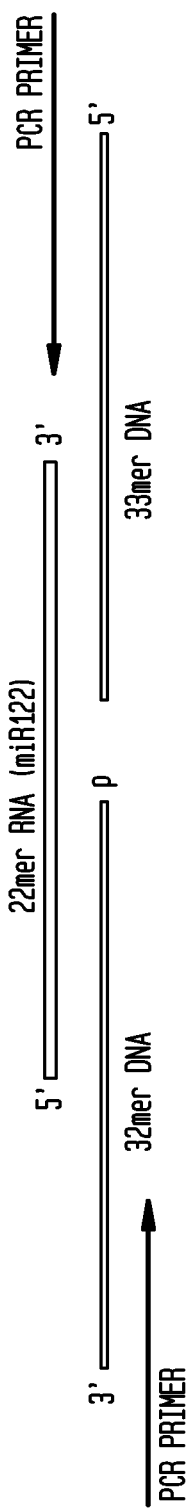

FIG. 10 shows the assay for detection of microRNAs using PBCV-1 ligase. A 5'-phosphorylated 32 nt DNA probe complementary to the 5' half of microRNA 122 and a 33 nucleotide DNA probe complementary to the 3' half of miR-122 miRNA are ligated together with PBCV-1 ligase after hybridization to target miRNA at concentrations. PCR primers re added and amplification performed.

Figure 11:
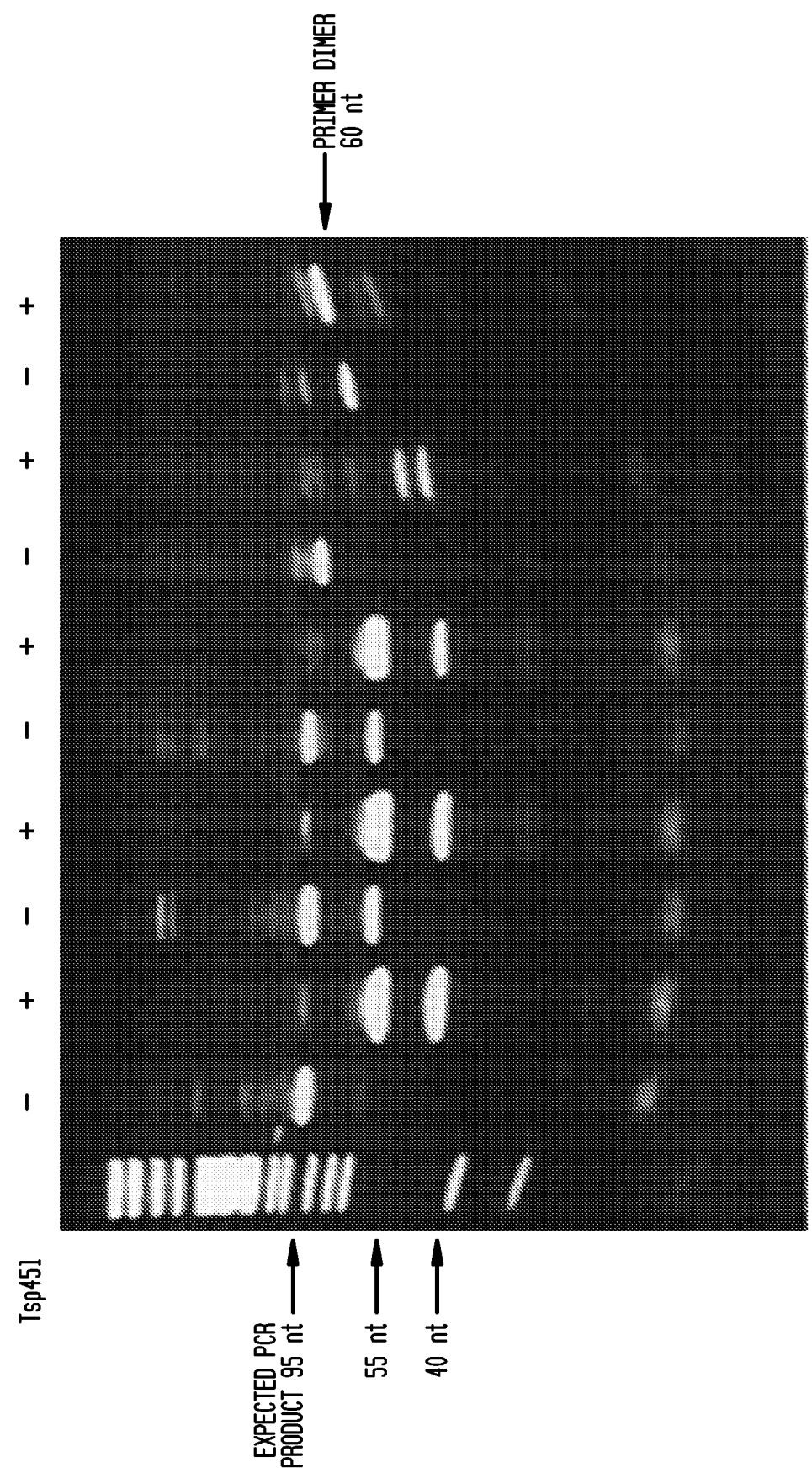

FIG. 11: Detection of miR-122 from total rat liver RNA by RNA splint ligation using PBCV-1 ligase.

DNA probes were hybridized to miR-122 in total rat liver RNA (about 50 pg miRNA/µg total RNA) and ligated by PBCV-1 ligase. The non-denaturing acrylamide gel shows undigested PCR products (−) and products digested with TSp45I (+), which cleaves the desired product specifically at GT(C/G)AC. A band of 95 bases that cleaves correctly in the presence of TSp45I, indicated by arrows, was found for the two rat liver RNA samples and in the positive control containing 0.1 pg of synthetic miR-122. The negative control, which contained no RNA, and HeLa cell RNA, which does not contain miR-122, have smaller PCR products that did not give the correct fragments when digested by Tsp45I.

Lanes were as follows:

| | |
|---|---|
| A | 1 µg Rat Liver RNA |
| B | 100 ng Rat Liver RNA |
| C | 0.1 pg miR-122 |
| D | 1 µg HeLa RNA |
| E | no RNA |

DETAILED DESCRIPTION

A ligase is described herein that surprisingly ligates ssDNA oligonucleotides splinted by a ssRNA with high efficiency. This ligation efficacy substantially improves the utility of techniques that preferably utilize RNA splinting with two or more oligonucleotides in methods such as RASL and RASL-seq as well as methods that enhance the utility of molecular inversion probes and modified ligase chain reaction/ligase detection reaction for RNA analysis and detection.

The term "RNA splint ligase" unless specified otherwise refers to an enzyme that is capable of ligating at least two ssDNA polynucleotides splinted by a complementary ssRNA polynucleotide and is capable of achieving ligation in less than 6 hours at molar concentrations of enzyme that are not absolutely required to be in molar excess compared to substrate. For very low concentrations of substrate, the enzyme may be in excess for convenience. Examples of RNA splint ligases are DNA ligases that are naturally occurring or closely related variants having at least 90%, 95%, 98% or 99% amino acid sequence identity to the wild type ligase where the ligase may be derived from algal viruses such as the *Chlorella* virus, for example, PBCV-1 ligase (SEQ ID NO:1), or may be identified by Blast search of the GenBank or NCBI or other database using for example, the basic local alignment search tool found on blast.ncbi.nlm.nih.gov/Blast.cgi using the query id gi|9632109|ref|NP_048900.1. as of Mar. 14, 2013 and variants and mutants thereof. The RNA splint ligase includes protein fusions including purification tags (e.g. HisTag, chitin binding domain (CBD), maltose binding protein (MBP), biotin) or DNA binding domain fusions (e.g. sso7d, or alkyl guanine transferase (AGT)).

The RNA splint ligase, single stranded polynucleotide and/or splint RNA may be immobilized on a matrix such as a reaction surface, or a magnetic bead to facilitate automated protocols and multiplexing reactions.

Contrary to the publication describing PBCV-1 ligase as inactive in ligating DNA oligonucleotides together on an RNA splint (Sriskanda, et al., (1998)), it has here been shown here that ssDNA oligonucleotides of a size greater than 8 nucleotides can surprisingly be ligated together to form a single oligonucleotide of at least 16 nucleotides when splinted by a complementary RNA with an efficiency that is greater than 10 fold to 1000 fold over T4 DNA ligase.

The term "RNA splint" includes a ssRNA having a size greater than 8 nucleotides or 10 nucleotides for example, greater than 12 or 15 or 18 or 20 or 22 or 24 or 26 or 28 or 100 nucleotides or a size as large as an RNA virus genome that is capable of hybridizing at least in part to at least two, three or more single stranded polynucleotides for example having a size of at least 8 or 10 or 12 or 14 or 16 or 20 nucleotides or greater in length so as to enable the ligation of the fragments to each other by means of an RNA splint ligase.

The RNA splint may be entirely complementary to the hybridizing polynucleotide, or may extend longer than the complementary region on the hybridizing polynucleotide, for example the splint may be 2, 4, 6, 8, 10 or more nucleotides longer than the hybridizing polynucleotide. The splint may be a portion of a much larger RNA structure for example an mRNA, tRNA, other cellular RNA, or RNA viral genome, such that a region of the RNA is complementary to the hybridizing polynucleotide but the majority of the structure has no complementarity to the hybridizing polynucleotide.

The RNA splint can come from any source. For example, splint RNA can be prepared by chemical synthesis or obtained from mRNA samples, total RNA, microRNAs, long noncoding RNAs or other naturally occurring RNAs, nucleic acid libraries, cells, cultures, tissues, pathogens, bodily fluids, urine, serum, biopsy samples, and environmental samples. Any other source of RNA that is known or can be developed can be used with the disclosed method.

The term "polynucleotide" includes DNA, RNA or part DNA and part RNA. The polynucleotides when used in a ligation reaction with an RNA splint are preferably single stranded and may be partially or wholly complementary to at least a portion of the RNA splint. An example of a polynucleotide described herein is a ssDNA oligonucleotide comprising at least 8 nucleotides.

Where the hybridizing polynucleotide has complementary regions to the RNA splint, this may be limited to the ligation junction with non-complementary regions elsewhere. Examples include primer binding regions for PCR amplification, self-complementary regions for reverse molecular beacon design, non-complementary linker regions, or non-complementary regions extending beyond the length of the RNA splint. The hybridizing polynucleotide may be linked together by a long non-complementary region such as for molecular inversion probes for rolling circle amplification (RCA), such that they are a single polynucleotide with two distinct hybridization regions. The polynucleotide may hybridize such that they are fully base paired to the splint at the ligation site with no gaps, or they may hybridize with a gap of for example 4, 6, 8, 10, or more nucleotides apart on the RNA splint such that ligation produces ssRNA loop-out region in the splint RNA.

One or more of the ss polynucleotides for hybridizing to the RNA splint, and/or RNA and/or RNA splint ligase may be coupled to a substrate for example, a matrix such as for example, a magnetic bead, a glass or silica substrate or a surface in a microfluidic device or other reaction chamber. Additional solid-state substrates to which oligonucleotides can be coupled, directly or indirectly include acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles (Pease, et al., *Proc. Natl. Acad. Sci. USA*, 91(11):5022-5026 (1994); Khrapko, et al., *Mol Biol (Mosk) (USSR)* 25:718-730 (1991); Stimpson, et al., *Proc. Natl. Acad. Sci. USA*, 92:6379-6383 (1995); Guo, et al., *Nucleic Acids Res.* 22:5456-5465 (1994); U.S. Pat. Nos. 5,871,928; 5,54,413; 5,429,807; 5,599,695; and 6,368,801)).

Coupling of polynucleotides to substrates may facilitate the handling of multiple samples singly or in multiplex reactions and in automation of the reaction. Suitable labels and capture tags used to identify products of ligation are known in the art and described in U.S. Pat. No. 6,368,801.

Features of ligating polynucleotides on an RNA splint may include one or more of the following:

Temperature range: Ligation may be achieved at a temperature in the range of 4° C. to 50° C. for example, 16° C., 25° C., and 37° C.

Enzyme concentrations: Ligation may be achieved at a concentration in the range of, for example, 1 nM-1 mM enzyme. Relatively small amounts of RNA splint ligase may be used to ligate ssDNA on an RNA splint with at least 70%, 80%, or 90% efficiency. Examples of substrate to enzyme ratios, include a range of 1:10 to 10:1 or 100:1 to 1:100 or 1:1000 to 1000:1 or 1:10,000 to 10,000:1 with completion of ligation within 6 hours, for example within 5 hours, 4 hours, 3 hours, 2 hours or 1 hour. Completion of ligation can be determined by PCR gel or capillary electrophoresis. T4 DNA ligase requires 10:1 to 100:1 of enzyme to substrate to obtain a reaction product and can take in excess of 12 hours to perform a ligation that may be incomplete. An example of the dramatic difference in activity between an RNA splint ligase and T4 DNA ligase and T4 RNA ligase is shown in FIG. 3(A)-3(B).

ATP concentrations: Ligation may be achieved in the presence of ATP in a range of less than 1.5 mM ATP for example, 1 µM-1 mM ATP, for example, 1 mM, 0.9 mM, 0.8 mM, 0.7 mM, 0.6 mM, 0.5 mM, 0.4 mM, 0.3 mM, 0.2 mM, 0.1 mM, 90 µM, 80 µM, 70 µM, 60 µM, 50 µM, 40 µM, 30 µM, 20 µM, 10 µM, or 1 µM. The use of ATP in the higher end of the range provided here may be preferred because if some hydrolysis of ATP occurs during storage or under reaction conditions, the buffer remains effective at stabilizing the RNA splint ligase reaction. Furthermore, reactions can be performed in the absence of ATP, if the RNA splint ligase exists in an adenylated form.

Reaction time: Ligation may be achieved in less than 12 hours. The reaction may be incubated for 5 minutes-60 minutes to achieve effective ligation or for longer periods of time as described above.

pH: Ligation may be achieved at a pH in the range of pH 6-pH 9, showing ligation rates for RNA splint ligases at least 10× faster than T4 DNA ligase within that range.

Ratio of reaction rates between T4 DNA ligase and an RNA splint ligase at high and low concentrations of ATP: In embodiments of the method, the rate of ligation at high ATP concentrations was consistently as much as 100:1 greater for an RNA splint ligase (PBCV-1 ligase) then for T4 DNA ligase or T4 RNA ligase regardless of substrate sequence. At low concentrations of ATP, under conditions optimized for T4 DNA ligase, the RNA splint ligase has at least fivefold or tenfold (10:1) greater activity than T4 DNA ligase.

Consistent improvement in ligation using RNA splint ligases compared with T4 DNA ligase with all substrates tested: The improved ligation as described above was independent of substrate sequence. This is in contrast with ligation reactions using T4 DNA ligase that was substrate sensitive. For example, T4 DNA ligase was able to ligate two oligonucleotides (SEQ ID NO:2 and SEQ ID NO:3) using an RNA splint (SEQ ID NO:4) in optimal conditions of low ATP albeit slowly whereas when the first nucleotide was changed from T to G in SEQ ID NO:3, the T4 DNA ligase in the same reaction conditions showed no detectable ligase activity. In contrast, the RNA splint ligase was able to ligate this altered substrate efficiently as well as the unaltered substrate.

Indeed, the rate of reaction difference between the best substrate and the worst substrate tested using T4 DNA ligase was greater than 1000 fold even using reported low concentrations of ATP for T4 DNA ligase (10 µM ATP versus 1 mM ATP).

Using the present embodiments with RNA splint ligase, the reaction difference between the same best substrate and the same worst substrate tested (as for T4 DNA ligase) using RNA splint ligase was less than 50 fold, for example (less than 40 fold, 30 fold or 20 fold) under the same reaction conditions as used for T4 DNA ligase.

The above-described characteristics of the RNA splint ligase for efficient ligation reactions between single stranded polynucleotides that are splinted by RNA can be used to enhance methods of RASL, RASL-seq, and Molecular Inversion Probes (also known as padlock probes). Other uses may include using RNA splints to help build-up long ssDNA through ligation of short fragments followed by RNase treatment (for example, using RNase H or mutants thereof) to remove the RNA splints (see FIG. 8(A)-8(B)) and detection of microRNAs (see FIGS. 10 and 11).

Quantitative mRNA profiling through RASL is generally accomplished through ligation of two ssDNA oligonucleotides (DNA probes) complementary to an RNA of interest. In standard RASL, cellular mRNA is isolated and treated with defined DNA probes that will anneal in the presence of the target mRNA sequence to form adjacent 5' and 3' DNA termini. The correctly annealed structure without gaps or mis-pairs can be ligated by the splint RNA ligase to form a ligated probe. The probes also contain qPCR primer regions adjacent to the RNA complementary region, such that when the two probes are ligated the product may be amplified, detected and quantified through qPCR. The degree of qPCR signal can be related to the quantity of the target RNA sequence in the original sample. Due to the strong preference of splint RNA ligase for correctly base paired sequences and sequences lacking gaps, splicing variants and single base polymorphisms in the target mRNA can be detected (Yeakley, et al., (2002)).

RASL-seq is a variant of RASL where detection is accomplished through total DNA sequencing. In RASL-seq the qPCR primer regions are replaced with PCR sequences suitable for amplification and sequencing by any high throughput DNA sequencing methodology. Hundreds of probe sets can be run in parallel with RASL-seq and thus expression levels of hundreds of genes can be simultaneously quantified (Li, et al., (2012)).

Through suitable design of probe sequence outside the mRNA complementary region, detection may be performed through other methods. One example is loop-mediated isothermal amplification (LAMP), wherein probes are designed to form LAMP target structures upon ligation (Notomi, et al., *Nucleic Acids Res.,* 28(12):e63 (2000)). Presence of target RNA is then detected via LAMP amplification, enabling advantages such as isothermal reaction conditions, rapid detection, and implementation in field or point-of-care diagnostics. Upon successful ligation, detection of amplification of target nucleic acid via may be performed with traditional qPCR dyes and probes as described above, or with additional methodologies: turbidity detection of precipitated magnesium pyrophosphate (Mori, et. al., *Biochem. Biophys. Res. Commun.,* 289:150-154 (2001)); colorimetric detection using metal-sensitive indicators (Tomita, et. al., *Nat. Protocols,* 3(5):877-82 (2008); Goto, et al., *BioTechniques,* 46(3):167-71 (2009)); bioluminescence detection by pyrophosphate conversion (Gandelman, et al., *PLoS One,* 5:e14155 (2010)); or detection via change in pH due to amplification in weakly-buffered conditions (Pourmand, et. al., *PNAS,* 103(17):6466-70 (2006); U.S. Pat. No. 7,888, 015; and U.S. patent application Ser. No. 13/799,995.

Molecular inversion probes use a single linear strand of DNA as the probe. Use of molecular inversion probes involves a DNA probe designed to have a complementary region to the RNA target sequence such that the 5' and 3' ends of the DNA anneal to bring the termini adjacent, forming a DNA/RNA hybrid helix connected by a loop of ssDNA. Ligation of the DNA termini in the presence of RNA complement by the RNA splint ligase forms a small circular DNA substrate for detection by, for example, RCA. Circularized DNA can be detected by either addition of RCA primers and amplification, or by removing the ssRNA through RNase treatment leaving the RNA/DNA hybrid region to act as a primer for RCA. RCA products can then be detected by turbidity, pH change, or readout of the DNA product via gel (Li, et al., *Anal. Chem.,* 81 (12):4906-4913 (2009); Absalan and Ronaghi, *Methods in Molecular Biology,* 396:315-330 (2007); Hardenbol, et al., (2003)).

Other examples of reactions that rely on RNA splinting which currently use T4 DNA ligase have been described in U.S. Pat. No. 6,368,801. These methods can be improved by replacing this enzyme with an RNA splint ligase include ligase chain reaction, ligation followed by PCR; the use of Padlock probes, and the use of FRET-detected molecular beacons generated by ligation (Peng, et al., *Anal Chem.*, 82(23):9727-35 (2010)).

All references cited herein are incorporated by reference.

EXAMPLES

Example 1

Assay of Ligation of DNA Oligonucleotide Substrates Using an RNA Splint

In Vitro Ligation Assay—

Ligase substrates were prepared from a variety of sequences. The sequences used as a standard were a 30 nt deoxynucleotide ssDNA fragment modified with a 5'-phosphate and a 3'-fluorophore (SEQ ID NO:3) and a 20 deoxynucleotide ssDNA acceptor fragment (SEQ ID NO:2) with unmodified termini annealed to an unmodified complementary strand composed of either DNA or RNA (SEQ ID NO:4). Ligations of 100 nM of the labeled, pre-annealed oligonucleotide structure were performed in ligation buffer (50 mM Tris pH 6-9, 10 mM MgCl$_2$, 1 mM DTT and 10 µM ATP-1 mM ATP) at 15° C.-40° C. The assay was initiated by addition of ligase (T4 DNA ligase or PBCV-1 ligase) to a final concentration between 10 pM and 10 µM and incubated at 16° C. or 20° C. Reactions were quenched with 100 mM EDTA, diluted to 1 nM in DNA with water, and analyzed by high throughput capillary electrophoresis.

Fragment Analysis by High Throughput Capillary Electrophoresis (CE)—

CE samples were prepared by dilution to 0.5 nM-2 nM in total FAM-label using ddH$_2$O. The GeneScan™ 120 LIZ® Size Standard (Applied Biosystems, Carlsbad, Calif.) was diluted 1:40 in formamide and 10 µl of this solution combined with 1 µl of each sample before application to either a 3130xl Genetic Analyzer (16 capillary array) or an 3730xl Genetic Analyzer (96 capillary array) (Applied Biosystems, Carlsbad, Calif.) at a 36 cm capillary length with POP7 polymer. Data was collected via Applied Biosystems Data Collection software and analyzed using PeakScanner™ software (V 1.0) (Applied Biosystems, Carlsbad, Calif.). The retention times and areas of all peaks in the blue (FAM) channel were recorded. Oligonucleotides (30-mer starting material, adenylylated 30-mer, and 50-mer ligation product) were identified by co-elution with synthetic standards. The fraction of each oligonucleotide in the sample was determined by dividing the peak area of each by the total peak area of all three oligonucleotides. The results are shown in FIG. 2(A)-2(D) for T4 DNA ligase and PBCV-1 ligase. The graphs in FIGS. 3-5 were determined from peak areas.

Example 2

Design of RASL Probes for Amplification

RASL probes (SEQ ID NO: 5)
L (/5phos/CGGTAAGACCTTTCGGTACTAGATCGGAAGAGCACAC);
and (SEQ ID NO: 6)
R (GGAAGCCTTGGCTTTTGGAACGTTGCGTCGAGTTTTC)

were designed to target the 3' region of the luciferase RNA (Promega, Madison, Wis.). Probes at 2.5 nM or 25 nM, with or without 2.5 nM luciferase RNA were mixed together in 25 µl of 1×T4 DNA ligase buffer (New England Biolabs, Ipswich, Mass.). The mix was heated to 65° C. for 10 minutes to denature the RNA and then at 45° C. for 60 minutes for the probe to anneal. Either 0.25 µg of PBCV-1 ligase or T4 DNA ligase (New England Biolabs, Ipswich, Mass. (M0202S, ~250 NEB units)) was added and the ligation mix was incubated at 37° C. for 60 minutes. 1 µl of the ligation mix was used for qPCR analysis using primers (GTGTGCTCTTCCGATCT (SEQ ID NO:7) and GGAAGCCTTGGCTTTTG (SEQ ID NO:8)) with Taq DNA polymerase using standard condition with PCR condition at 95° C. for 2 minutes and then 50 cycles at 95° C. for 10 minutes, 52° C. for 15 minutes and 68° C. for 30 minutes. The results are shown in FIG. 7.

Here, in the absence of template, the background signal using PBCV-1 ligase is reduced compared to T4 DNA ligase where at least 10% and as many as 50% (5-15 cycles) more thermocycles would be required during PCR amplification before a background signal was detected.

Where a positive signal from amplification of an RNA splint ligated DNA was detected, this occurred after 10%-50% (5-15) fewer cycles of amplification than would a positive signal using T4 DNA ligase for the same DNA.

Example 3

Characterization of PBCV-1 Ligase in a Comparison with T4 DNA Ligase at Varying Concentrations of Ligase and ATP FIG. 4(A)-4(B) shows the results of reacting 10 pM-10 µM PBCV-1 ligase or T4 DNA ligase with oligonucleotide substrates (shown in FIG. 9) in a standard ligase buffer containing 1 mM ATP or a modified buffer in which the amount of ATP was reduced to 10 µM ATP for 15 minutes at 37° C. At T4 DNA ligase concentrations >1 µM, most of the substrate is converted to AppDNA regardless of ATP concentration.

The results shown in FIG. 4(A)-4(B) demonstrate that as much as 100 fold or greater improvement in ligation efficiency was observed for PBCV-1 ligase in contrast to T4 DNA ligase for buffer containing standard amounts of ATP (1 mM). In non-optimal buffer containing only 10 µM ATP which increased T4 ligase activity, there was still at least 100 fold improvement in PBCV-1 ligase activity compared with T4 ligase activity using the standard substrate.

Example 4

Determining Splice Variants for a Single Gene

Oligonucleotides that hybridize to each exon in a gene can be prepared. Different combinations of oligonucleotides can be mixed together and ligation allowed to occur. QPCR on the ligation products will permit determination of the frequency of different splice variants. For example, if a gene has 10 exons, hybridize DNA encoding exon 1 with exons 2-10 where each of 2-10 have a separate detectable label. Perform ligation using an mRNA splint and determine the representation of splice variants.

Example 5

MicroRNA Detection by Splint Ligation

Detection of miR-122 by splint ligation using PBCV-1 ligase.

FIG. 10 outlines the assay for detection of microRNA by ligation followed by PCR amplification. Either synthetic miR-122 5'pUGGAGUGUGACAAUGGUGUUUG (SEQ ID NO:9) (0.1 pg), total rat liver RNA (1 μg or 100 ng), or 1 μg total Hela cell RNA, was hybridized with two DNA probes (1 ng each) that were complementary to miRNA-122, with sequences pGTCACACTCCTCTGAGTCGGAGA-CACGCAGGG (SEQ ID NO:10) and CCTCTC-TATGGGCAGTCGGTGATAAACACCATT (SEQ ID NO:11). The RNA and DNA oligos were heat denatured at 85° C. and then slowly cooled. The ligation (containing 1 μM PBCV-1 ligase and 1×T4 DNA ligase buffer (New England Biolabs, Ipswich, Mass.) in addition to the probes and RNA source in total volume of 10 μl) was incubated at 16° C. for 2 hours. 5 μl of the ligation mixture was amplified in a 25 μl reaction with two PCR primers; CCATCTCATC-CCTGCGTGTCTCCGACTCAG (SEQ ID NO:12) and CCACTACGCCTCCGCTTTCCTCTCTATGGGCA-GTCGGTGAT (SEQ ID NO:13) and 12.5 μl of OneTaq® DNA polymerase master mix (New England Biolabs, Ipswich, Mass.). The PCR reaction was carried out for 25 cycles. FIG. 11 shows the results of use with biological samples. In this example, the identity of the PCR product was confirmed by digesting DNA with the restriction enzyme, Tsp45I. This enzyme cleaves DNA at GT(C/G)AC found in the miR-122 sequence. The digested and undigested PCR products were separated on a non-denaturing acrylamide gel and stained with ethidium bromide. The expected product band of 95 bases was observed in the two rat liver RNA samples and in the positive control containing 0.1 pg synthetic miR-122. This experiment demonstrates that microRNAs from biological samples can be detected by RNA splint ligation using PBCV-1 followed by PCR to enhance sensitivity.

---

What is claimed is:

1. A method for ligating DNA polynucleotide sequences, comprising:
   (a) obtaining RNA from a sample that comprises cells or a bodily fluid to produce an RNA sample comprising naturally-occurring RNAs;
   (b) hybridizing at least two DNA polynucleotide sequences to a naturally-occurring RNA in the RNA sample;
   (c) ligating the at least two DNA polynucleotide sequences to one another using a ligase that has an amino acid sequence that is at least 90% identical to the *Chlorella* virus PBCV-1 ligase of SEQ ID NO:1: and
   (d) detecting the product of step (c).

2. The method of claim 1, wherein the naturally-occurring RNA is a miRNA, long non-coding RNA, mRNA or tRNA.

3. The method of claim 1, wherein the ligation of step (c) is a done in a buffer comprising 1 μM to 1.5 mM ATP.

4. The method of claim 1, wherein the product of step (c) is circular.

5. The method of claim 1, wherein the product of step (c) is linear.

6. The method of claim 1, wherein at least 70% of the hybridized oligonucleotides are ligated together within 6 hours.

7. The method of claim 1, wherein the ligating of step (c) is at least 10 times faster than using T4 DNA ligase with same molar ratio enzyme to substrate an ATP at a concentration of 1 μM to 1.5 mM.

8. The method of claim 1, wherein the ligase is the *Chlorella* virus PBCV-1 ligase of SEQ ID NO:1.

9. The method of claim 1, wherein the method comprises:
   (i) hybridizing at least two DNA polynucleotide sequences to the naturally-occurring RNA;
   (ii) adding the ligase to the hybridized DNA oligonucleotides; and
   (iii) ligating the at least two DNA polynucleotide sequences to one another using the ligase added in (ii).

10. The method of claim 1, further comprising amplifying the product of step (c).

11. The method of claim 10, wherein the amplifying is done by PCR.

12. The method of claim 10, wherein the amplifying is done by rolling circle amplification.

13. The method of claim 1, wherein the naturally-occurring RNA is complementary to at least 8 nucleotides of each of the at least two DNA polynucleotide sequences.

14. The method of claim 1, wherein the ligase that has an amino acid sequence that is at least 95% identical to the *Chlorella* virus PBCV-1 ligase of SEQ ID NO:1.

* * * * *